United States Patent [19]

Zaiger

[11] Plant 4,362

[45] Jan. 2, 1979

[54] NECTARINE TREE

[76] Inventor: C. Floyd Zaiger, 537 Rosemore Ave., Modesto, Calif. 95351

[21] Appl. No.: 840,241

[22] Filed: Dec. 12, 1977

[51] Int. Cl.[2] ..... A01H 5/03
[52] U.S. Cl. ..... Plt./41
[58] Field of Search ..... Plt./41

*Primary Examiner*—Robert E. Bagwill

*Assistant Examiner*—James R. Feyrer

[57] ABSTRACT

A variety of nectarine tree which is of large size, vigorous upright growth, being a productive and regular bearer of large size, firm, yellow-flesh, clingstone fruit having yellow skin substantially overspread with red. The fruit is further characterized by its good eating quality and the high degree of firm flesh, and the ability to ship long distance markets.

4 Drawing Figures

ORIGIN OF THE VARIETY

The new variety of nectarine tree was developed by me in my experimental orchard located near Modesto, Calif., as a second generation seedling of a cross between Red Grand Nectarine (U.S. Plant Pat. No. 1,060) and an open pollinated seedling from Gold King Nectarine (U.S. Plant Pat. No. 1,424).

ASEXUAL REPRODUCTION OF THE VARIETY

The present variety of nectarine tree was asexually propagated by budding and grafting, as performed by me at Modesto, California, shows that such reproductions run true to the original tree in all respects.

SUMMARY OF THE VARIETY

The herein claimed variety of nectarine tree is of large size, vigorous, upright in growth, and a productive and regular bearer of large size, late ripening, clingstone fruit having firm, yellow flesh and a high degree of red skin color. The fruit ripening and harvested in the same maturity season as Gold King Nectarine (U.S. Plant Pat. No. 1,424). The present variety of nectarine tree is further characterized by having fruit with a higher degree of red skin color than other late maturing varieties. The fruit colors nearly 2 weeks before ripening having firm flesh with good shipping quality.

PHOTOGRAPHS OF VARIETY

The accompanying photographs show typical specimens of the foliage and fruit of my new variety, with upper and lower surfaces of the foliage being illustrated and a fruit divided on its suture plane to reveal flesh coloration and showing a stone remaining in place. The illustrations were taken shortly after being picked at maturity (shipping ripe) and the colors are as nearly true as reasonably possible in a color representation of this type.

DESCRIPTION OF THE VARIETY

The botanical details of this new and distinct variety of nectarine tree with color terminology (except those in common terms) in accordance with Reinhold Color Atlas by A. Kornerup and J. H. Wanscher.

Tree:
- *Size.*—Large.
- *Vigor.*—Vigorous.

- *Form.*—Upright.
- *Production.*—Productive.
- *Density.*—Dense.
- *Bearing.*—Regular.

Trunk:
- *Size.*—Medium stocky.

Branches:
- *Size.*—Medium stocky.
- *Lenticels.*—Medium size. Medium number.
- *Texture.*—Smooth to medium rough.

Leaves:
- *Size.*—Average length 6". Average width 1½".
- *Form.*—Lanceolate. Acutely pointed.
- *Color.*—Upper surface — (28-E-7) to (28-F-7). Lower surface — (28-D-6) to (28-E-6).
- *Margin.*—Crenate.
- *Texture.*—Smooth.
- *Petiole.*—Medium length.
- *Glands.*—Average number 4, alternate. Large, reniform.

Flower buds:
- *Size.*—Medium.
- *Length.*—Medium.

Flowers:
- *Blooming period.*—Mar. 3, 1976 to Mar. 15, 1976.
- *Size.*—Large, showy.

Fruit:
- *Maturity when described.*—Hard ripe.
- *Date of first picking.*—Aug. 17, 1976.
- *Date of last picking.*—Aug. 27, 1976.
- *Size.*—Comparatively uniform. Large. Average diameter axially 2⅝". Average transversely in suture plane — 2⅝".
- *Form.*—Globose.
- *Suture.*—Shallow, extends from base to apex.
- *Ventral surface.*—Usually rounded, varies from equal to unequal.
- *Cavity.*—Rounded. Average depth — ½". Average breadth — 1".
- *Apex.*—Short to slightly retuse.

Skin:
- *Thickness.*—Thick to medium.
- *Texture.*—Tough, tenacious to flesh.
- *Tendency to crack.*—None.
- *Down.*—Wanting.
- *Color.*—Yellow ground color (4-A-8) to (4-B-8). Red blush covering most of the surface (8-A-8) to (9-B-8).

Flesh:

*Juice.*—Moderate.

*Texture.*—Firm, meaty.

*Ripens.*—Even.

*Flavor.*—Subacid.

*Aroma.*—Very little.

*Eating quality.*—Good.

*Color.*—Yellowish orange (4-A-7) to golden yellow (5-A-6).

Stone:

*Type.*—Clingstone; adheres to flesh over entire surface.

*Fibers.*—Short.

*Size.*—Medium. Average length — $1\frac{3}{8}''$. Average width — $\frac{7}{8}''$. Average thickness — $\frac{1}{2}''$.

*Form.*—Mostly obovate, tip acuminate.

*Base.*—Mostly straight.

*Sides.*—Mostly equal.

*Surfaces.*—Irregularly furrowed toward apex, pitted toward base.

*Color.*—Light brown (8-D-7) to (8-C-7).

*Tendency to split.*—Slight.

Use: Market, local and long distance. Dessert.

Shipping and keeping quality: Very good.

The tree and its fruit herein described may vary in slight detail due to climatic and soil conditions under which the variety may be grown. The description is that of the variety produced under ecological conditions prevailing at Modesto, Calif., and the characteristics are found to hold true in asexual reproduction of the variety.

The following is claimed:

1. A new and distinct variety of nectarine tree, as illustrated and described, which is a regular and productive bearer of large size, clingstone fruit, with firm flesh, attractive red skin color and of good eating quality; and fruit is further characterized in comparison to Gold King Nectarine by having smoother skin, a higher degree of red skin color, more uniform ripening and better shipping and storage quality.

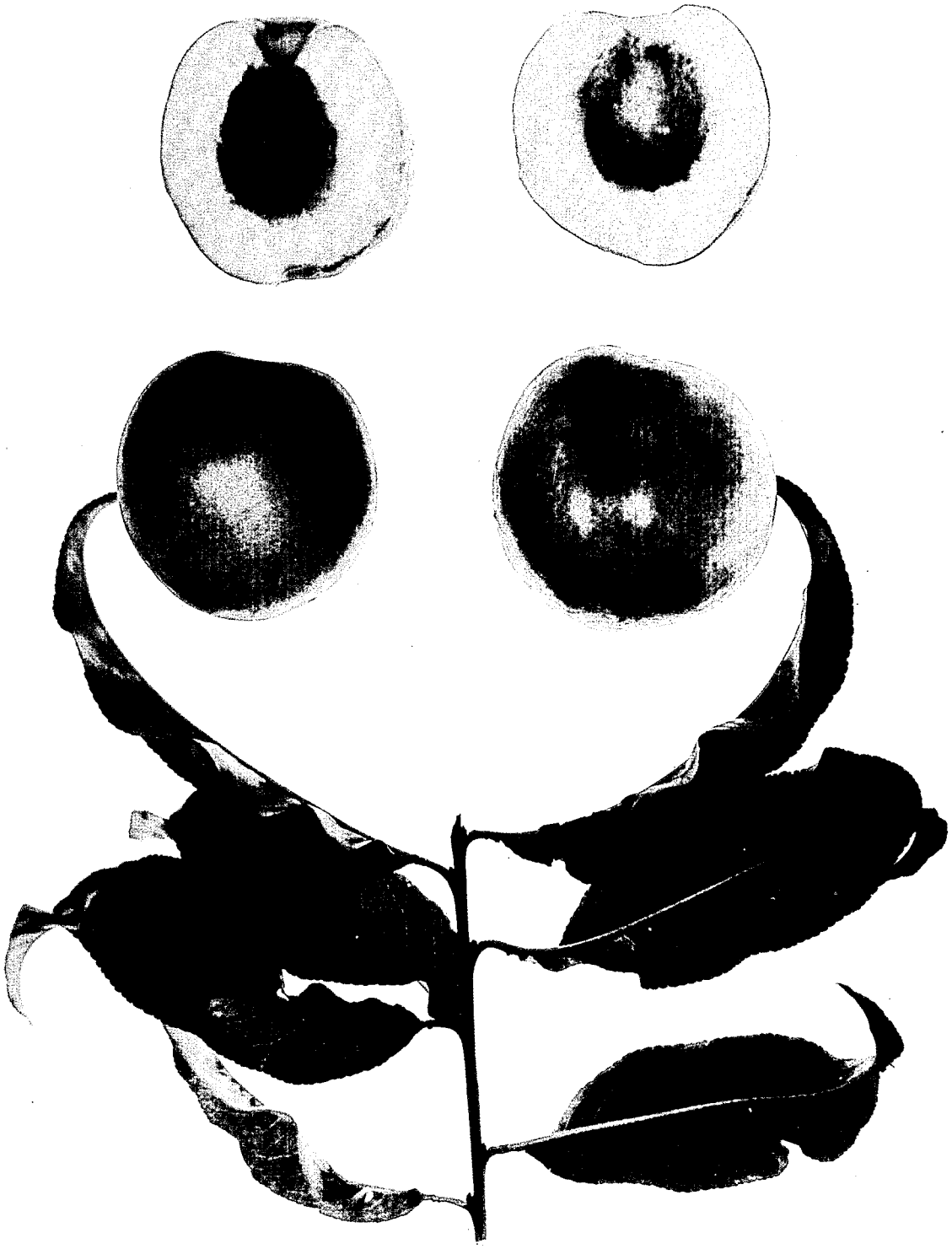

* * * * *